United States Patent [19]
Dolfini

[11] 4,098,999
[45] Jul. 4, 1978

[54] CERTAIN 2-SUBSTITUTED CEPHALOSPORINS

[75] Inventor: Joseph E. Dolfini, Princeton, N.J.

[73] Assignee: E. R. Squibb & Sons, Inc., Princeton, N.J.

[21] Appl. No.: 499,368

[22] Filed: Aug. 21, 1974

Related U.S. Application Data

[60] Division of Ser. No. 298,172, Oct. 16, 1972, Pat. No. 3,852,282, which is a continuation-in-part of Ser. No. 812,386, Apr. 1, 1969, abandoned.

[51] Int. Cl.² ............................................ C07D 501/20
[52] U.S. Cl. ........................................ 544/15; 544/22; 544/23; 544/24; 544/25; 544/28; 544/29; 544/30
[58] Field of Search ...................... 260/243 C; 544/15

[56] References Cited

U.S. PATENT DOCUMENTS

| 3,578,660 | 5/1971 | Cooper | 260/243 C |
| 3,660,395 | 5/1972 | Wright et al. | 260/243 C |
| 3,923,795 | 12/1975 | Spry | 260/243 C |

Primary Examiner—Paul M. Coughlan, Jr.
Attorney, Agent, or Firm—Lawrence S. Levinson; Merle J. Smith; Stephen B. Davis

[57] ABSTRACT

Disclosed herein are novel analogs of cephalosporins. They differ from prior art compounds in that they are substituted in the 2-position and can be prepared by reacting known cephalosporins with an active source of halogen to form a 2-halogenated intermediate. Substitution of the thus formed intermediate can be accomplished with various substitutents. The compounds of this invention are useful antimicrobial and antibacterial agents.

20 Claims, No Drawings

CERTAIN 2-SUBSTITUTED CEPHALOSPORINS

This application is a division of Ser. No. 298,172 filed on Oct. 16, 1972, now U.S. Pat. No. 3,852,282, which in turn was a continuation-in-part of Ser. No. 812,386 filed on Apr. 1, 1969, now abandoned.

This invention relates to $\Delta^3$-cephems having the formula:

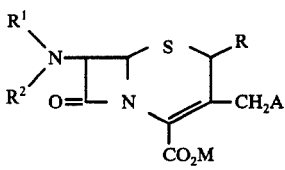

wherein: R is iodo, chloro, bromo, lower alkoxy, lower alkenyloxy, lower alkynyloxy, aryloxy, lower alkanoyloxy, lower alkylthio, lower alkylenylthio, lower alkynylthio, arylthio, aroylthia or lower alkanoylthia; $R^1$ and $R^2$, A and M are as hereinafter described. These compounds of this invention, wherein iodo, chloro and bromo are in the 2-position, are considered to be intermediates in the preparation of the end products.

For purposes of this invention the following definitions are applicable: lower alkyl, lower alkenyl and lower alkynyl are straight or branched chains substituted hydrocarbon radicals of from 1 to about 8 carbons, with the preferred radicals having from 1 to 5 carbons; aryl as employed herein is intended to mean phenyl, and substituted phenyl; and acyl is a carboxylic acid radical of from 1 to 8 carbons.

The term substituted means lower alkyl, lower alkoxy, amino, lower alkylamino, dilower alkylamino, halo, lower alkylthio, hydroxy, cyano, nitro, trifluoromethyl or acyloxy.

The terms aroyloxy, lower alkanoyloxy, thia-aroyl and thia-lower alkanoyl are intended to mean

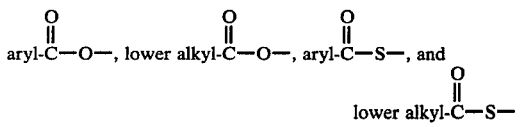

respectively.

The compounds of the invention are prepared by reacting a $\Delta^3$-cephem compound with an active source of halogen to yield the corresponding cephalosporin substituted in the 2-position with a chloro, bromo, or iodo. This intermediate is highly reactive and may be readily modified by displacement of the halogen by a nucleophilic species of formula:

$$HYR^4$$

wherein $R^4$ is lower alkyl, lower alkenyl, lower alkynyl, aryl or acyl, and Y is oxygen or sulfur.

An active source of halogen may be utilized in the practice of this invention. Examples of those which may be utilized are N-bromosuccinimide, N-chlorosuccinimide, sulfuryl chloride, t-butylhypochlorite, molecular iodine, molecular bromine, and so forth.

The cephems which may be utilized in the practice of this invention have the formula:

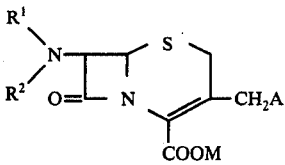

wherein A is hydrogen, acetoxy, or a quaternary ammonium radical, e.g., pyridinium, or when taken together with M, a monovalent carbon-oxygen bond; and M is hydrogen, a pharmaceutically acceptable nontoxic cation, an anionic charge when A is a quaternary ammonium radical, a readily hydrolyzable ester, such as a benzyl, t-butyl, trimethylsilyl or trichloroethyl, or when taken together with A, a monovalent carbon-oxygen bond; $R^1$ and $R^2$ are hydrogen, acyl or triaryl lower alkyl; wherein acyl is

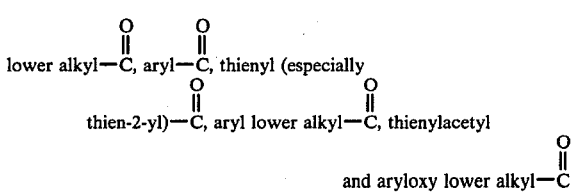

and when $R^1$ and $R^2$ are acyl, the $R^1R^2N$ group is a succinimido and phthalimido.

Compounds wherein $R_1$, $R_2$ are hydrogen may be prepared by either of two routes:

(1) cleavage of a phthalimide compound wherein $R^1R^2N$ is phthalimido by hydrazine or, (2) cleavage of a 7-aroylamino compound wherein $R^1$ is hydrogen and $R^2$ is benzoyl by the method shown in Australian Pat. No. 19,902/62.

These amines are converted to the amides of this invention by the standard acylation reactions described in R. R. Chauvette, E. H. Flynn, B. G. Jackson, E. R. Lavagnino, R. B. Morin, R. A. Mueller, R. P. Pioch, R. W. Roeske, C. W. Ryan, J. L. Spencer, and E. Van Heyningen, J. Amer. Chem. Soc., 84, 3401 (1962); E. Van Heyningen, J. Med. Chem., 8, 22 (1965); E. Van Heyningen and C. N. Brown, ibid., 8, 174 (1965); J. L. Spencer, F. Y. Siu, E. H. Flynn, B. G. Jackson, M. V. Sigal, H. M. Higgins, R. R. Chauvette, S. L. Andrews, and D. E. Bloch, Antimicrob. Ag. Chemother., 1967, 573; J. L. Spencer, F. Y. Siu, B. G. Jackson, H. M. Higgins, and E. H. Flynn, J. Org. Chem., 32, 500 (1967); L. B. Crast, Jr., and J. M. Essery, U.S. Pat. No. 3,352,858 (1967); J. L. Spencer, E. H. Flynn, R. W. Roeske, F. Y. Siu, and R. R. Chauvette, J. Med. Chem., 9, 746 (1966); M. Kurita, S. Atarashi, K. Hattori, and T. Tokano, J. Antibiot., Ser. A, 19, 243 (1966), R. B. Morin, B. G. jackson, R. A. Mueller, E. R. Lavagnino, W. B. Scanlon, and S. L. Andrews, J. Amer. Chem. Soc., 85, 1896 (1963); E. Van Heyningen, Advances in Drug Research, Academic Press, New York (1967), Vol. 4, "Cephalosporins," pp. 1–70.

The salts of the new compounds are metal salts, above all, the salts of therapeutically useful metals of the groups of alkali metals or alkaline earth metals such as sodium, potassium, ammonium or calcium or salts with organic bases, for example, with triethylamine, N-ethylpiperidine, dibenzylethylenediamine, N,N'-bis-(dehydroabiethyl)ethylenediamine or procaine or others such as are known to be useful for preparing salts of penicillins or cephalosporins.

The new compounds are very stable towards penicillinases. Under the conditions of therapeutic application they are stable. They display antibacterial activity towards Gram-positive bacteria, for example, *Staphylococcus aureus,* and especially towards penicillin-resistant strains but above all, towards Gram-negative bacteria, for example, *Escherichia coli, Klebsiella pneumoniae, Salmonella typhosa* and *Bact. proteus.* They may therefore be used for combating infections caused by grampositive or gram-negative micro organisms, and also as additives for animal feedstuffs and in the preservation of foodstuffs or as disinfectants. For these purposes they are administered in the same way as other semi-synthetic cephalosporins for instance 7-(thienylacetylamino)-cephalosporanic acids.

Hitherto, there has been no attempt to halogenate the cephalosporin starting materials of this invention in view of the unsaturation in the 3-position. Therefore, it was not expected that this reaction would yield the 2-halo semi-synthetic cephalosporanic acid of this invention in a relatively good yield.

The reaction between the cephalosporin derivative and the halogenating agent is carried out under ambient conditions and may require a free radical source or initiator such as azobis (isobutyronitrile), benzoyl peroxide, and so forth.

The reaction between the 2-halogenated intermediate and HYR$^4$ is advantageously carried out in the presence of an organic nitrogen base, for example, triethylamine, in the presence of an inert solvent, for example, dimethylformamide, methylene chloride, tetrahydrofuran or acetonitrile.

Suitable reagents which may be utilized having the formula: HYR$^4$ are phenol; o-methylphenol; o-propylphenol, thiophenol, m-cyanophenol, p-chlorophenol, ethylthio, t-butylthio, p-hydroxyphenol, 4-methylphenol, cresol, o-nitrophenol, o-trifluoromethylphenol, 4-butylthiophenol, t-butylalcohol, heptanol, isopropanol, benzyl alcohol, 2-methoxynaphthol, α-methoxy-3, 4-dichlorophenyl acetic acid, pyridyl-3-acetic acid, butylthioacetic acid, acetic acid, and so forth.

The following examples illustrate the invention, all temperatures being in degrees Centigrade:

EXAMPLE 1

7-Phthalimido-3-acetoxy methyl-Δ$^3$-cephem-4-carboxylic acid

A solution of 2.13 g. of 7-aminocephalosporanic acid and 2.3 g. of sodium bicarbonate in 80 ml. of acetone-water (1:1) is cooled to 5° C.; a solution of 2.04 g. of phthaloyl chloride in 20 ml. of acetone is slowly added over about a ten-minute interval. After vigorous agitation for 1.5 hours at 5° C., the reaction mixture is diluted with 50 ml. water and the pH adjusted to 8 with a small amount of aqueous sodium bicarbonate solution. The solution is extracted with ethyl acetate and then acidified with ice-cold aqueous 10% hydrochloric acid to pH 2. Extraction with 50 ml. of ethyl acetate isolates the product; after drying over sodium sulfate, the solution is filtered and evaporated at reduced pressure at ambient temperature. The residue of crude product, 1.2 g., solidifies on standing. Trituration with cold ether leaves a purified material, 0.8 g. The infrared spectrum showed in chloroform absorption maxima at 5.60 μ. and 5.75–5.80 μ.

EXAMPLE 2

Methyl ester of 7-phthalimido-3-acetoxy methyl-Δ$^3$-cephem-4-carboxylic acid

A solution of the product obtained from Example 1 in dioxane is treated with an excess of ethereal diazomethane. After allowing the reaction to proceed to completion, acetic acid is added to destroy any excess diazomethane. Ether is then added to dilute the solution, which is followed by washing with successive treatments of dilute aqueous sodium bicarbonate and cold 2% aqueous hydrochloric acid. The ethereal solution is dried with sodium sulfate and evaporated. The residue is triturated with ether. The thus formed ester, when recrystallized from acetone hexane, is a pure white solid with a m.p. of 159° C.

EXAMPLE 3

7-Phthalimido-3-hydroxymethyl-Δ$^3$-cephem-4-carboxylic acid, γ lactone

A solution of 405 mg. of 7-phthalimido-3-acetoxymethyl-Δ$^3$-cephem-4-carboxylic acid in 10 ml. of acetone-water (1:1) is acidified with 10 ml. of concentrated hydrochloric acid and placed under a nitrogen atmosphere. After stirring at room temperature for 20 hours, the precipitated product is separated by filtration. Crystallization from aqueous acetone yields the pure material occurring as white needles, m.p. 270° C. The infrared spectrum (KBr) showed maxima at 1795, 1768, 1715 cm$^{-1}$.

EXAMPLE 4

7-Phthalimido-3-hydroxymethyl-2-bromo-Δ$^3$-cephem-4-carboxylic acid, γ-lactone.

A suspension of 68 mg. of 7-phthalimido-3-hydroxymethyl-Δ$^3$-cephem-4-carboxylic acid γ-lactone, 36 mg. of N-bromosuccinimide and about one mg. of azo-bis-(isobutyronitrile) in 25 ml. pure chloroform (purified by distillation from phosphorous pentoxide) is placed under a nitrogen atmosphere and stirred at room temperature for 1 hour. Thin layer chromatography (ethanol/benzene on silica gel) indicated the absence of starting materials. The solution is washed with ice-cold 5% aqueous sodium bicarbonate, then dried with sodium sulfate, filtered and evaporated at reduced pressure at ambient temperature. The product is obtained as a powdery solid in nearly quantitative yield. Purification is effected by crystallization of a sample from acetone-ether, a white solid, m.p. 222°–224° C., being obtained.

EXAMPLE 5

7-Phthalimido-3-hydroxymethyl-2-methoxy-Δ$^3$-cephem-4-carboxylic acid, γ-lactone A suspension of 150 mg. of 7-phthalimido-3-hydroxymethyl-2-bromo-Δ$^3$-cephem-4-carboxylic acid, γ-lactone in 30 ml. of methanol is stirred at ambient temperature. The reaction mixture is maintained at a neutral pH by the addition of triethylamine. After the reaction is completed, the solution is evaporated at reduced pressure. The residue is taken up in chloroform and washed with water, dilute aqueous hydrochloric acid and dilute aqueous sodium bicarbonate, then dried over sodium sulfate and evaporated at reduced pressure. The residue crude product is purified by chromatography on 20 g. of Florisil. The column is developed with benzene-chloroform (1:1) and the pure product subsequently removed by elution with methanol-chloroform (1:9). The product crystallized from methanol yields a cream-colored solid, m.p. 187°–190° C.

EXAMPLE 6

Methyl-3-(acetoxymethyl)-2-bromo-7-phthalimido-$\Delta^3$-cephem-4-carboxylic acid, methyl ester 416 Mg. of methyl ester of 3-(acetoxymethyl)-7-phthalimido-$\Delta^3$-cephem-4-carboxylic acid in 50 ml. of pure chloroform (purified by distillation from phosphorous pentoxide) is treated with 178 mg. of N-bromosuccinimide and about three mg. azo-bis(isobutyronitrile) under a nitrogen atmosphere at room temperature until thin layer chromatography showed the absence of starting material. The reaction mixture is chilled both to below 5° C. and washed with ice-cold aqueous 5% sodium bicarbonate and then dried with sodium sulfate, filtered, and evaporated at reduced pressure at about ambient temperature to recover the desired product for further reactions.

EXAMPLE 7

2-Methoxy-3-(acetoxymethyl)-7-phthalimido-$\Delta^3$-cephem-4-carboxylic acid, methyl ester A suspension of 200 mg. of 3-(acetoxymethyl)-2-bromo-7-phthalimido-$\Delta^3$-cephem-4-carboxylic acid, methyl ester in 40 ml. of methanol is stirred at room temperature for two hours with the addition of triethylamine being used to maintain a neutral solution. After the reaction is completed, the solution is evaporated at reduced pressure; the residue is taken up in ethyl acetate and the solution washed with cold aqueous 5% sodium bicarbonate, cold aqueous 5% hydrochloric acid, saturated aqueous sodium chloride. After drying over sodium sulfate, the solution is evaporated at reduced pressure at ambient temperature. The product is deposited as a powdery solid.

EXAMPLE 8

2-Bromo-7-phenylacetylaminocephalosporanic acid

One millimole of the 7-phenylacetylaminocephalosporanic acid and one millimole of N-bromosuccinimide in 50 ml. of chloroform (purified by distillation from phosphorous pentoxide) are stirred with 3–4 mg. of azo-bis(isobutyronitrile) at room temperature under nitrogen. The crude product is obtained by evaporating the chloroform solution and triturating the residue with hexane, an amorphous powder results.

EXAMPLE 9

Reacting equimolar quantities of 2-bromo-7-phenylacetylamino-cephalosporanic acid and ethanol in the presence of triethylamine at a neutral pH in THF, the product is 2-ethoxy-7-phenylacetylamino-cephalosporanic acid.

EXAMPLE 10

Following the procedure of Example 8 but utilizing 7-benzoamidocephalosporanic acid in lieu of 7-phenylacetylamino-cephalosporanic acid, the product recovered is 2-bromo-7-benzamido-cephalosporanic acid.

EXAMPLE 11

Following the procedure of Example 9 but utilizing 2-bromo-7-benzamidocephalosporanic acid in lieu of 2-bromo-7-phenylacetylamino-cephalosporanic acid the product obtained is 2-ethoxy-7-benzamidocephalosporanic acid.

EXAMPLE 12

Utilizing triethylamine salt of acetic acid in dimethylformamide in lieu of ethanol in the procedure of Example 9, the product formed is 2-(acetoxy)-7-phenylacetylamino-cephalosporanic acid.

EXAMPLE 13

Phenol is reacted with 2-bromo-3-methyl-7-phenylacetamido-cephalosporanic acid, methyl ester under conditions similar to those set forth in Example 9, the product formed is 2-phenoxy-3-methyl-7-phenylacetamido-cephalosporanic acid, methyl ester.

EXAMPLE 14

Following the procedures of Example 9 but utilizing S-phenylthioacetic acid in lieu of ethanol the product recovered is 2[S-phenylthioacetyl]-7-phenylacetylamino-cephalosporanic acid, methyl ester.

EXAMPLE 15

Utilizing thiophenol in lieu of ethanol in Example 9, the product recovered is 2-phenylthio-7-phenylacetylamino-cephalosporanic acid.

EXAMPLE 16

2-Chloro-7-thienylacetylamino-cephalosporanic acid

One millimole of 7-thienylacetylamino-cephalosporanic acid and one millimole of sulfuryl chloride in 50 ml. of chloroform (purified by distillation from phosphorous pentoxide) are stirred with 3–4 mg. of azo-bis(isobutyronitrile) at room temperature under nitrogen. The crude product is obtained by evaporating by washing the chloroform solution and triturating the residue with hexane.

EXAMPLE 17

Desacetoxy-7-aminocephalosporanic acid (1.65 gms.) is utilized in lieu of 7-aminocephalosporanic acid of Example 1 and utilizing the procedures therein the product obtained is 7-phthalimido-3-methyl-$\Delta^3$-cephem-4-carboxylic acid.

EXAMPLE 18

Utilizing the procedure of Example 2 but substituting 7-phthalimido-3-methyl-$\Delta^3$-cephem-4-carboxylic acid in lieu of 7-phthalimido-3-acetoxymethyl-$\Delta^3$-cephem-4-carboxylic acid, the product formed is the methyl ester of 7-phthalimido-3-methyl-$\Delta^3$-cephem-4-carboxylic acid.

EXAMPLE 19

Following the procedure of Example 6 but utilizing 7-phthalimido-3-methyl-$\Delta^3$-cephem-4-carboxylic acid, methyl ester in lieu of 3-(acetoxymethyl-7-phthalimido-$\Delta^3$-cephem-4-carboxylic acid, methyl ester, the product formed is 2-bromo-3-methyl-7-phthalimido-$\Delta^3$-cephem-4-carboxylic acid, methyl ester.

EXAMPLE 20

Following the procedure of Example 7 but utilizing 2-bromo-3-methyl-$\Delta^3$-cephem-4-carboxylic acid, methyl ester in lieu of 3-(acetoxymethyl)-2-bromo-7-phthalimido-$\Delta^3$-cephem-4-carboxylic acid, methyl ester, the product formed is 2-methoxy-3-methyl-7- phthalimido-$\Delta^3$-cephem-4-carboxylic acid, methyl ester.

EXAMPLE 21

2-Methoxy-7-amino-cephalosporanic acid

One millimole of 2-methoxy-3-(acetoxymethyl)-7-benzamido-$\Delta^3$-cephem-4-carboxylic acid in 35 ml. absolute methylene chloride is treated with 79 mg. of pyridine and 150 mg. of trimethylchlorosilane added. After a short time (ca. 15 minutes), 1.2 g. of additional pyridine is added, followed by 832 mg. of phosphorous pentachloride at about 30° C. After 1 hour, the reaction vessel is chilled in an ice-salt bath, and 15 ml. of methanol added, the reaction mixture is stirred at −10° C. for 30 minutes, then at 25° ± 5° C. for 30 minutes. Four ml. of 25% aqueous formic acid is added and the pH adjusted to 2.0 with triethylamine and the mixture filtered. After one-half hour, the pH is raised to about 3.5 until the amino acid precipitates. It is filtered off and washed with methanol to recover the desired product.

EXAMPLE 22

2-Methoxy-7-amino-3-methyl-$\Delta^3$-cephem-4-carboxylic acid

Substitution of 2-methoxy-7-benzamido-3-methyl-$\Delta^3$-cephem-4-carboxylic acid in lieu of 2-methoxy-3-(acetoxymethyl)-7-benzamido-$\Delta^3$-cephem-4-carboxylic acid in Example 21 gives the desired product.

EXAMPLES 23–36

7-Acylamido-2-halo-cephalosporins (Table I)

General Procedure

A mixture of 1 mole of 7-acylamido substrate selected from group I and 1 m mole of the indicated halogenating agent from group II in 100 ml. of pure chloroform (freshly distilled from $P_2O_5$) is treated with a few crystals of azo-bis - isobutyronitrile and placed under an inert (nitrogen or argon) atmosphere. The reaction mix is stirred for 6 to 8 hours at room temperature, then washed with cold 5% aqueous sodium bicarbonate solution, dried ($Na_2SO_4$), filtered and evaporated to deposit the product indicated in compound III.

EXAMPLES 37–53

7-Acylamido-2-substituted-cephalosporins (Table II)

General Procedure

A mixture of the product selected from column 1 of Table II is dissolved in the solvent indicated. The substrate to be added is selected from column 2. An equivalent of base is added over a 45 minute period. After a total elapsed reaction time of 1.5 hours, the product (3) is isolated by evaporating the solvent, taking the residue up in ethylacetate or ether, working with cold 1% aqueous sodium bicarbonate, followed by cold 1% aqueous hydrochloric acid, and saturated salt solution, drying ($Na_2SO_4$) and evaporating at reduced pressure.

Table I

| | I | | | II | III |
|---|---|---|---|---|---|
| | M | A | | Halogenating Reagent | R |
| 23 | phthalimido | $OCH_3$ | H | N-bromo-succinimide | Br |
| 24 | phthalimido | $OCH_3$ | $CH_3CO_2$ | N-bromo-succinimide | Br |
| 25 | phthalimido | $C_6H_5CH_2O$ | H | N-bromo-succinimide | Br |
| 26 | phthalimido | $(CH_3)_3SiO$ | H | N-bromo-succinimide | Br |
| 27 | phthalimido | HO | H | N-bromo-succinimide | Br |
| 28 | phthalimido | | O | N-bromo-succinimide | Br |
| 29 | phthalimido | | O | $SO_2Cl_2$ | Cl |
| 30 | phthalimido | | O | $(CH_3)_3C-OCl$ | Cl |
| 31 | $C_6H_5CH_2\overset{O}{\overset{\|}{C}}NH$ | | O | $(CH_3)_3C-OCl$ | Cl |
| 32 | $C_6H_5OCH_2\overset{O}{\overset{\|}{C}}NH$ | | O | N-bromo-succinimide | Br |
| 33 | thien-2-yl $CH_2\overset{O}{\overset{\|}{C}}NH$ | | O | N-bromo-succinimide | Br |
| 34 | $CH_3\overset{O}{\overset{\|}{C}}NH$ | | O | N-bromo-succinimide | Br |
| 35 | $CH_3\overset{O}{\overset{\|}{C}}NH$ | $CH_3O$ | H | $SO_2Cl_2$ | Cl |
| 36 | $CH_3\overset{O}{\overset{\|}{C}}NH$ | $C_6H_5CH_2O$ | $CH_3CO_2$ | $SO_2Cl_2$ | Cl |

Table II

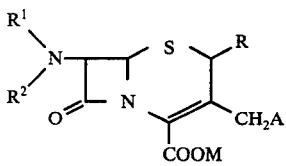

| | R¹ | R² | M¹ | A | R | Solvent Substrate | 2 R | 3 |
|---|---|---|---|---|---|---|---|---|
| 37 | phthalimido | | | O | Br | CH₃OH | None | CH₃O |
| 38 | phthalimido | | | O | Br | C₂H₅OH | None | n-C₂H₅O |
| 39 | phthalimido | | | O | Br | n-C₄H₉OH | None | n-C₄H₉O |
| 40 | phthalimido | | | O | Br | Dioxane | C₆H₅SH | C₆H₅S |
| 41 | phthalimido | | | O | Br | Dioxane | n-C₄H₉S | n-C₄H₉SH |
| 42 | phthalimido | | | O | Br | Dioxane | CH₃SH | CH₃S |
| 43 | phthalimido | | | O | Br | Dioxane | CH₂=CHCH₂SH | CH₂=CH—CH₂S |
| 44 | C₆H₅CH₂CONH | | CH₃O | H | Cl | Dioxane | CH₂=CHCH₂SH | CH₂=CH—CH₂S |
| 45 | CH₃CONH— | | CH₃O | CH₃CO₂ | Cl | Dioxane | CH₂=CHCH₂SH | CH₂=CH—CH₂S |
| 46 | thien-2-yl CH₂CONH— | | HO | CH₃CO₂ | Cl | Dimethoxy-thane | CH₂=CHCH₂SH | CH₂=CH—CH₂S |
| 47 | thien-2-yl CH₂CONH— | | HO | CH₃CO₂ | Cl | Dimethoxy-thane | Allyl Alcohol | CH₂=CH—CH₂O |
| 48 | thien-2-yl CH₂CONH— | | HO | CH₃CO₂ | Cl | Dimethoxy-thane | CH₃C≡C—CH₂OH | CH₃C≡C—CH₂O |
| 49 | phthalimido | | | O | Br | acetonitrile | CH₃CO₂H | CH₃CO₂— |
| 50 | phthalimido | | | O | Br | acetonitrile | C₆H₅CO₂H | C₆H₅CO₂— |
| 51 | phthalimido | | | O | Br | acetonitrile | CH₃CO₂H | CH₃CO₂— |
| 52 | C₆H₅OCH₂CONH | | C₆H₅CH₂O | H | Cl | CH₂Cl₂ | CH₃CO₂H | CH₃CO₂— |
| 53 | C₆H₅OCH₂CONH | | C₆H₅CH₂O | H | Cl | CH₂Cl₂ | CH₃CO₂H | CH₃CO₂— |

What is claimed is:
1. A compound of the formula

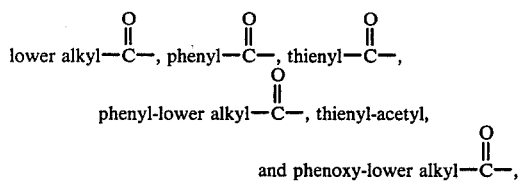

wherein A is selected from the group consisting of hydrogen, acetoxy, hydroxy, and pyridinium and when taken together with M, a monovalent carbon-oxygen bond; M is selected from the group consisting of hydrogen, sodium, potassium, ammonium, calcium, triethylamine, N-ethylpiperidine, dibenzylethylenediamine, N,N'-bis(dehydroabietyl)ethylenediamine, procaine, benzyl, trimethylsilyl, t-butyl, trichloroethyl, an anionic charge when A is pyridinium, and when taken together with A, a monovalent carbon-oxygen bond; $R^1$ and $R^2$ are both hydrogen, or $R^2$ is hydrogen and $R^1$ is selected from the group consisting of lower alkyl—$\overset{O}{\underset{\|}{C}}$—, phenyl—$\overset{O}{\underset{\|}{C}}$—, thienyl—$\overset{O}{\underset{\|}{C}}$—, phenyl-lower alkyl—$\overset{O}{\underset{\|}{C}}$—, thienyl-acetyl, and phenoxy-lower alkyl—$\overset{O}{\underset{\|}{C}}$—, or $R^1$ and $R^2$ taken together with the nitrogen atom to which they are attached form succinimido or phthalimido; and R is selected from the group consisting of lower alkoxy, phenoxy, lower alkenyloxy, lower alkynyloxy, lower alkylthio, phenylthio, lower alkenylthio and lower alkynylthio.

2. The compound of claim 1 wherein R is lower alkoxy.

3. The compound of claim 1 wherein R is phenoxy.

4. The compound of claim 1 wherein R is lower alkylthio.

5. The compound of claim 2 having the name 7-phthalimido-3-hydroxymethyl-2-methoxy-Δ³-cephem-4-carboxylic acid, γ-lactone.

6. The compound of claim 2 having the name 7-phthalimido-3-(acetoxymethyl)-2-methoxy-Δ³-cephem-4-carboxylic acid, methyl ester.

7. The compound of claim 2 having the name 7-phthalimido-3-methyl-2-methoxy-Δ³-cephem-4-carboxylic acid, methyl ester.

8. The compound of claim 2 having the name 7-amino-2-methoxy-cephalosporanic acid.

9. The compound of claim 2 having the name 7-amino-2-methoxy-3-methyl-Δ³-cephem-4-carboxylic acid.

10. The compound of claim 2 having the name 2-ethoxy-7-phenylacetylamino-cephalosporanic acid.

11. The compound of claim 2 having the name 2-ethoxy-7-benzamido-cephalosporanic acid.

12. The compound of claim 3 having the name 3-methyl-2-phenoxy-7-phenylacetamido-cephalosporanic acid, methyl ester.

13. The compound of 1 having the name 2-phenylthio-7-phenylacetylamino-cephalosporanic acid.

14. The compound of claim 1 having the name 2-phenylthio-7-phthalimido-Δ³-cephem-4-carboxylic acid, γ-lactone.

15. The compound of claim 4 having the name 2-methylthio-7-phthalimido-Δ³-cephem-4-carboxylic acid, γ-lactone.

16. The compound of claim 4 having the name 2-butylthio-7-phthalimido-Δ³-cephem-4-carboxylic acid, γ-lactone.

17. The compound of claim 1 having the name 2-allylthio-7-phthalimido-$\Delta^3$-cephem-4-carboxylic acid, γ-lactone.

18. The compound of claim 1 having the name 2-allylthio-7-phenylacetylamino-3-methyl-$\Delta^3$-cephem-4-carboxylic acid, methyl ester.

19. The compound of claim 1 having the name 2-allylthio-7-acetylamino-cephalosporanic acid, methyl ester.

20. The compound of claim 1 having the name 2-allylthio-7-(2-thienyl)acetylamino-cephalosporanic acid.

* * * * *

UNITED STATES PATENT AND TRADEMARK OFFICE
CERTIFICATE OF CORRECTION

PATENT NO. : 4,098,999
DATED : July 4, 1978
INVENTOR(S) : Joseph E. Dolfini

It is certified that error appears in the above-identified patent and that said Letters Patent are hereby corrected as shown below:

Col. 1, line 23, "described. These" should read, -- described. Those --.

Col. 2, line 57, "jackson," should read -- Jackson, --.

Col. 8, line 6 should read -- A mixture of 1 m mole --.

Cols. 9 and 10 in Table II, the headings should read as follows:

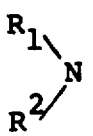

[SEAL]

Attest:

RUTH C. MASON
Attesting Officer

Signed and Sealed this

Fifth Day of December 1978

DONALD W. BANNER
Commissioner of Patents and Trademarks